United States Patent [19]

Kojima et al.

[11] Patent Number: 5,298,488
[45] Date of Patent: Mar. 29, 1994

[54] CM-CHITIN DERIVATIVES AND USE THEREOF

[75] Inventors: Masayoshi Kojima, Minami-Ashigara; Hiroyuki Komazawa, Kanagawa, both of Japan

[73] Assignee: Fuji Photo Film Co., Ltd., Kanagawa, Japan

[21] Appl. No.: 780,790

[22] Filed: Oct. 23, 1991

[30] Foreign Application Priority Data

Oct. 26, 1990 [JP] Japan ................................. 2-89491
Nov. 30, 1990 [JP] Japan ................................. 3-33718
Mar. 29, 1991 [JP] Japan ................................. 66-156

[51] Int. Cl.$^5$ .................. A61K 37/02; C07K 5/08; C07K 7/06; C07K 9/00
[52] U.S. Cl. .................... 514/8; 424/450; 530/322; 530/345
[58] Field of Search ................ 530/322, 345; 930/DIG. 500; 514/8, 55, 822; 424/450

[56] References Cited

U.S. PATENT DOCUMENTS

| | | | |
|---|---|---|---|
| 4,326,532 | 4/1982 | Hammar | 514/56 |
| 4,703,039 | 10/1987 | Hawlger et al. | 530/333 |
| 4,952,562 | 8/1990 | Klein et al. | 530/331 |
| 4,988,621 | 1/1991 | Ruoslahti et al. | 435/240.2 |

*Primary Examiner*—Jeffrey E. Russel
*Attorney, Agent, or Firm*—Sughrue, Mion, Zinn Macpeak & Seas

[57] ABSTRACT

A CM-chitin derivative which has, as an essential unit, a cohesive peptide represented by the following general formula (I), bonded to the side chain of CM-chitin, wherein the bond connecting CM-chitin and said peptide is selected from the group consisting of an amido bond, an ester bond, an ether bond and a urethane bond:

$$-[R^1]-[CO]-([X]-Arg-Gly-Asp-[Y])_n-[Z]-[R^2]-\ldots \quad (I)(SEQ\ ID\ NO:1)$$

wherein the bracket [ ] means that the corresponding group or residue may be present or absent and if they are present, X and Y each represents an amino acid residue selected from the group consisting of Ser, Gly, Val, Asn and Pro or a peptide residue; Z represents —O— or —NH—; one of $R^1$ and $R^2$ represents a hydrogen atom, or a substituted or unsubstituted alkyl group having 1 to 9 carbon atoms or aryl group having 6 to 9 carbon atoms and the other represents a hydrogen atom, a linear or branched alkylene group having 1 to 9 carbon atoms or an arylene group having 6 to 9 carbon atoms wherein the alkylene and arylene groups may have substituents; and n is an integer ranging from 1 to 5. The derivative or salt thereof is useful as an effective component of compositions for inhibiting adhesion of animal cells or for inhibiting coagulation of blood platelets.

18 Claims, No Drawings

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Arg  Gly  Asp
    1

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Arg  Gly  Asp  Arg  Gly  Asp
    1                   5

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Arg  Gly  Asp  Arg  Gly  Asp  Arg  Gly  Asp
    1                   5

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Arg Gly Asp Arg Gly Asp Arg Gly Asp Arg Gly Asp Arg Gly Asp
1               5                   10                  15

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Arg Gly Asp Ser Gly
1               5

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Gly Arg Gly Asp Ser Pro
1               5

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Arg Gly Asp Ser
1

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Gly Arg Gly Asp Ser
1               5

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Gly Asp Ser Gly
1

CM-CHITIN DERIVATIVES AND USE THEREOF

BACKGROUND OF THE INVENTION

The present invention relates to CM-chitin derivatives having a tripeptide, Arg-Gly-Asp (SEQ ID NO: 1), as an essential unit, and salts thereof, as well as a composition for inhibiting adhesion of animal cells and a composition for inhibiting coagulation of blood platelets.

Fibronectin is a protein involved in the cell-extracellular substrate adhesion and is likewise thought to be involved in coagulation of blood platelets and the metastasis of cancer. These interactions are mediated by a series of receptors present in the cell surface region. It is confirmed that these receptors can specifically recognize an amino acid sequence: Arg-Gly-Asp (SEQ ID NO: 1) of the fibronectin although the fibronectin is a macromolecule having a molecular weight of about 250,000 and it has been reported that the sequence plays an important role in the interaction between the receptors and the fibronectin (Nature, 1984, 309, p. 30). Since then, there have been many studies conducted in which an oligopeptide or polypeptide having such an amino acid sequence: Arg-Gly-Asp (SEQ ID NO: 1) is used.

There have been various studies reported, such as a method for inhibiting the coagulation of blood platelets by the use of various linear and cyclic oligopeptides having an Arg-Gly-Asp (SEQ ID NO: 1) sequence (Polymer Preprints, Japan, 1989, 38, p. 3149; Japanese Unexamined Patent Publication (hereinafter referred to as "J. P. KOKAI") No. Hei 2-174797); a method in which a peptide having an Arg-Gly-Asp (SEQ ID NO: 1) sequence is used as a cell movement-inhibiting agent (J. P. KOKAI No. Hei 2-4716); and a method using as a cell-adhesive membrane, a PMMA film on which Arg-Gly-Asp (SEQ ID NO: 1) sequences are immobilized (Polymer Preprints, Japan, 1988, 37, p. 705). In addition, J. P. KOKAI Nos. Hei 1-309682 and Hei 1-305960 disclose a method which comprises peptides having Arg-Gly-Asp (SEQ ID NO: 1) sequences as essential structural units covalently bonded to a polymer and the resulting product is used as a substrate for cultivating animal cells or for biological composite artificial organs and J. P. KOKAI No. Sho 64-6217 discloses a method in which a polypeptide having Arg-Gly-Asp-Ser (SEQ ID NO: 7) sequences is used as a platelet protective agent for blood taken out of the body. Further, there is a known method comprising inhibiting the metastasis of cancer by the use of an oligopeptide having Arg-Gly-Asp (SEQ ID NO: 1) sequences or a polypeptide having the sequence as repeating units (Int. J. Biol. Macromol., 1989, 11, p. 23; ibid, 1989, 11, p. 226; Jpn. J. Cancer Res., 1989, 60, p. 722).

Chitin is a polysaccharide in which N-acetyl-D-glucosamine is linked through the β- (1→4) bond and is a main component of the exoskeleton of Crustacea and Insects. It is widely distributed in lower animals and invertebrates and serves to support and/or protect the organs. The functions thereof correspond to those of cellulose in the plant. Chitin is also called the last biomass, derivatives thereof have been variously studied recently and, in particular, many studies concerning solvent-soluble chitin derivatives have been reported. Among them, CM-chitin in which a carboxymethyl group is bonded to the C-6 hydroxyl group is water-soluble and a very important compound as a starting material for preparing various chitin derivatives. Chitin and derivatives thereof are detailed in "Applications of Chitin Chitosan", edited by the Society for research of chitin chitosan published by Gihodo Publishing Company and "The Last Biomass: Chitin Chitosan", edited by the same Society, published by Gihodo Publishing Company.

The CM-chitin causes deacetylation during carboxylation and this indicates the presence of an amino group in addition to a carboxyl group. The amino group thereof can easily undergo carboxylation with a dibasic acid or a derivative thereof, preferably a polybasic acid anhydride. The N, O-sulfation of the CM-chitin is also easy. However, there is no known compound in which an oligopeptide having an Arg-Gly-Asp (SEQ ID NO: 1) sequence as an essential unit or a polypeptide having the sequences as repeating unit. If such an oligopeptide or a polypeptide is introduced into a compound, it would be expected that the ability of bonding thereof to a receptor and the stability thereof in blood would be greatly enhanced.

Accordingly, an object of the present invention is to provide a novel CM-chitin derivative.

Another object of the present invention is to provide a composition for inhibiting adhesion of animal cells containing the chitin derivative as an effective component.

A further object of the present invention is to provide a composition for suppressing coagulation of blood platelets which comprises the novel CM-chitin derivative as an effective component.

According to an aspect of the present invention, a CM-chitin derivative is provided having, as an essential structural unit, an adhesive peptide represented by the following general formula (I) through any one of an amido bond, an ester bond, an ether bond and a urethane bond on the side chain and salts thereof:

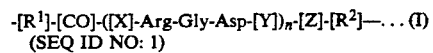
(SEQ ID NO: 1)

In general formula (I), [ ] means that each corresponding group or residue may be present or absent and if they are present, X and Y each represents an amino acid residue selected from the group consisting of Ser, Gly, Val, Asn and Pro or a peptide residue consisting of two or more of the amino acids; Z represents —O— or —NH—; one of $R^1$ and $R^2$ represents a hydrogen atom, a linear or branched alkyl group having 1 to 9 carbon atoms or an aryl group having 6 to 9 carbon atoms in which the alkyl and aryl groups may be substituted and the other represents a hydrogen atom, a linear or branched alkylene group having 1 to 9 carbon atoms or an arylene group having 6 to 9 carbon atoms wherein the alkylene and arylene groups may be substituted; and n is an integer ranging from 1 to 5.

Examples of substituents for $R^1$ and $R^2$ include halogen atoms, carbonyl, carboxyl, amino, hydroxyl, sulfo, aryl, nitro and cyano groups, unsaturated hydrocarbon group which has a double bond and triple bond and they may have two or more substituents.

According to another aspect of the present invention, there is provided a composition for inhibiting adhesion of animal cells or for suppressing coagulation of blood platelets comprising the foregoing CM-chitin derivative as an effective component.

DESCRIPTION OF THE PREFERRED EMBODIMENTS

The present invention relates to a CM-chitin derivative in which an adhesive peptide having, as an essential unit, an Arg-Gly-Asp (SEQ ID No: 1) sequence is covalently bonded to a sulfated CM-chitin, carboxylated CM-chitin or CM-chitin. The molecular weight of the CM-chitin derivatives is not more than 200,000, in particular, 3,000 to 100,000 and the derivative is preferably soluble in water at room temperature.

Examples of carboxylating agents used herein are succinic anhydride, maleic anhydride, phthalic anhydride, itaconic anhydride, citraconic anhydride, pyromellitic anhydride and trimellitic anhydride. Amino acids used in the adhesive peptide may be either L- or D-isomers and preferably L-isomers.

Examples of the salts of the CM-chitin derivatives of the invention are those with inorganic acids such as hydrochlorides, sulfates, nitrates, phosphates and borates; and those with organic acid s such as acetates, trifluoroacetates, trifluoromethanesulfonates, lactates and tartrates.

Methods for synthesizing these peptides are not restricted to specific ones and may be liquid phase and solid phase methods and those in which an automatic synthesizer is employed. These synthesis methods are detailed in, for instance, Lectures on Biochemical Experiments, "Chemistry of Proteins IV", pp. 207–495, edited by Biochemical Society of Japan, published by Tokyo Kagaku Dojin Publishing Company; Lectures on Biochemical Experiments, Second Series, "Chemistry of Proteins (the last volume)", edited by Biochemical Society of Japan, published by Tokyo Kagaku Dojin Publishing Company; and "Fundamental Knowledge and Experiments of Peptide Synthesis", edited by Izumiya et al., published by Maruzen Publishing Company. Alternatively, it is also possible to use commercially available synthetic peptides.

Amide bond-forming methods in which agents such as cyanogen bromide, acid azides or water-soluble carbodiimides can be used for coupling the CM-chitin or carboxylated CM-chitin with an adhesive peptide.

The CM-chitin derivatives of the invention have a core sequence: Arg-Gly-Asp (SEQ ID No: 1) of a cell-cohesive protein and are adhered to cells through the core sequence according to a mechanism similar to that for the cell-adhesive protein. For this reason, they serve as agonists or antagonists of the cell-adhesive protein which exhibit a variety of biological activities such as immunoregulating action, wound-healing action, action for inhibiting platelet coagulation observed in blood vessels and nervous disorder-healing action.

Thus, at least one of the CM-chitin derivatives of the invention can be administered to patients together with commonly used optional carriers or pharmaceutical auxiliary agents in the form of wound-healing agents, immunoregulating agents or platelet coagulation-inhibiting agents. In particular, the derivatives are preferably used as animal cell adhesion-inhibiting agents or platelet coagulation-inhibiting agents. The dose thereof varies depending on various factors such as conditions to be treated, age and weight of patients and generally ranges from 0.2 μg/kg to 400 mg/kg.

The CM-chitin derivatives may be administered through various routes which are generally used for the administration of peptide-containing medicines. For instance, they are preferably administered parenterally, intravenously, intramuscularly and subcutaneously. In the preparation of injectable pharmaceutical preparations containing the same, the chitin derivative is dissolved in, for instance, PBS or physiological saline to give an injectable solution. These pharmaceutical preparations may comprise a commonly used stabilizer such as glycine and albumin. Moreover, the chitin derivative may be parenterally administered by encapsulating them in liposomes to give microcapsules. Further, if they are formulated in the form of, for instance, suppository, sublingual tablets and nasal sprays, they can be absorbed through mucous other than digestive tracts.

The present invention will hereinafter be explained in more detail with reference to the following non-limitative working Examples and Preparation Examples, but the present invention is by no means limited to these specific Examples.

Preparation Example 1: Synthesis of Cohesive Peptide by Solid

Phase Method

Synthesis of this peptide was performed using a peptide synthesizer according to the Merrifield System. α-Amino groups were protected with Boc, the resulting peptide was purified by preparative high performance liquid chromatography (HPLC) after separating from the solid phase of a resin to give an adhesive synthetic peptide showing a single peak.

| Name | Adhesive Peptides Synthesized | | |
|---|---|---|---|
| | Structural Formula | Sequence No. | Yield |
| Peptide-1 | H—(Arg—Gly—Asp)—OH | (SEQ ID NO: 1) | 37% |
| Peptide-2 | H—(Arg—Gly—Asp)$_2$—OH | (SEQ ID NO: 2) | 28% |
| Peptide-3 | H—(Arg—Gly—Asp)$_3$—OH | (SEQ ID NO: 3) | 19% |
| Peptide-4 | H—(Arg—Gly—Asp)$_5$—OH | (SEQ ID NO: 4) | 11% |

Preparation Example 2: Syntheses of Peptide-5: H-(Arg-Gly-Asp-Ser-Gly)-NH$_2$ (SEQ ID NO: 5)

The peptide-5 was prepared by a liquid phase method according to a sequential-extension method.

(1) Synthesis of Boc Ser(Bzl)GlyNH$_2$

To 400 ml of CH$_2$Cl$_2$, there was dissolved 59 g (0.2 mole) of Boc Ser(Bzl) and then 41.2 g (0.2 mole) of DCC was added thereto with ice-cooling. A solution of 22.1 g of GlyNH$_2$ . HCl in 400 ml of CH$_2$Cl$_2$ which was then neutralized by the addition of 20.2 g of N-methylmorpholine under ice-cooling was added to the resulting solution. The mixture was stirred for 3 hours under ice-cooling and then at room temperature overnight. After separating precipitates formed by filtration, the filtrate was concentrated under reduced pressure and then the residue obtained was dissolved in ethyl acetate. The solution was washed, in turn, with an NaHCO$_3$ aqueous solution, 1M citric acid aqueous solution and then an NaCl aqueous solution, dried over Na$_2$SO$_4$ and evaporated to dryness under reduced pressure to give 58.3 g (yield 83%) of a product as white powder.

(2) Synthesis of BocAsp(OBzl)Ser((Bzl)GlyNH$_2$ (SEQ ID NO: 1)

There was added 400 ml of TFA/CH$_2$Cl$_2$ (=1/1) to 56.2 g (0.16 mole) of BocSer((Bzl)GlyNH$_2$, the resulting mixture was stirred at room temperature for one hour and the TFA and CH$_2$ Cl$_2$ were removed by concentration under reduced pressure followed by dissolution in ethyl acetate, neutralization with an aqueous solution of NaHCO$_3$ and washing with an aqueous solution of NaCl. After drying the solution over Na$_2$ SO$_4$, the ethyl acetate was removed by distillation under reduced pressure.

There were dissolved the resulting compound and 51 7 g (0.16 mole) of BocAsp (Obzl) in 800 ml of CH$_2$ Cl$_2$ followed by addition of 33 g (0.16 mole) of DCC under ice-cooling, stirring for 3 hours and further at room temperature overnight. After distilling off the CH$_2$ Cl$_2$ under reduced pressure, the resulting residue was dissolved in ethyl acetate. The solution was washed, in turn, with an NaHCO$_3$ aqueous solution, 1M citric acid aqueous solution and then an NaCl aqueous solution, dried over Na$_2$ SO$_4$ and evaporated to dryness under reduced pressure to give 71.2 g (yield 80%) of a product as white powder.

(3) Synthesis of BocGlyAsp(Obzl)Ser((Bzl)GlyNH$_2$ (SEQ ID NO: 9)

There was added 400 ml of TFA/CH$_2$ Cl$_2$ (=1/1) to 66.7 g (0.12 mole) of BocAsp(Obzl)Ser((Bzl)GlyNH$_2$ (SEQ ID NO: 1), the resulting mixture was stirred at room temperature for one hour and the TFA and CH$_2$ Cl$_2$ were removed by concentration under reduced pressure followed by dissolution in ethyl acetate, neutralization with an aqueous solution of NaHCO$_3$ and washing with an aqueous solution of NaCl. After drying the solution over Na$_2$ SO$_4$, the ethyl acetate was removed by distillation under reduced pressure.

There were dissolved the resulting compound and 51.7 g (0.12 mole) of BocGly in 700 ml of CH$_2$ Cl$_2$ followed by addition of 24.7 g (0.12 mo)e) of DCC under ice-cooling, stirring for 3 hours and further at room temperature overnight. After removing the resulting DCurea by filtration and distilling off the CH$_2$ Cl$_2$ under reduced pressure, the resulting residue was dissolved in ethyl acetate. The solution was washed, in turn, with an NaHCO$_3$ aqueous solution, 1M citric acid aqueous solution and then an NaCl aqueous solution, dried over Na$_2$ SO$_4$ and evaporated to dryness under reduced pressure to give 61.8 g (yield 84%) of a product as white powder.

Synthesis of BocArg(Mts)GlyAsp(Obzl)Ser((Bzl)GlyNH$_2$ (SEQ ID NO: 5)

There was added 400 ml of TFA/CH$_2$Cl$_2$ (=1/1) to 61.3 g (0.1 mole) of BocGlyAsp(Obzl)Ser((Bzl)-GlyNH$_2$ (SEQ ID NO: 9), the resulting mixture was stirred at room temperature for one hour and the TFA and CH$_2$ Cl$_2$ were removed by concentration under reduced pressure followed by dissolution in ethyl acetate, neutralization with an aqueous solution of NaHCO$_3$ and washing with an aqueous solution of NaCl. After drying the solution over Na$_2$ SO$_4$, the ethyl acetate was removed by distillation under reduced pressure.

There was dissolved the resulting compound and 45.6 g (0.1 mole) of BocArg(Mts) (Mts: a mesitylene-2-sulfonyl group) in 800 ml of DMF followed by addition of 22.5 g (0.1 mole) of DCC and 14 g (0.1 mole) of HOBt under ice-cooling, stirring for 3 hours and further at room temperature overnight. After removing the resulting Dcurea by filtration and distilling off the solvent under reduced pressure, the resulting residue was dissolved in ethyl acetate. The solution was washed, in turn, with an NaHCO$_3$ aqueous solution, 1M citric acid aqueous solution and then an NaCl aqueous solution, dried over Na$_2$ SO$_4$ and evaporated to dryness under reduced pressure to give 42.8 g (yield 45%) of a product as white powder.

(5) Removal of Protective Groups (Synthesis of Peptide-5)

To a solution of BocArg(Mts)GlyAsp(Obzl-)Ser((Bzl)GlyNH$_2$ (SEQ ID NO:5) (5 g; 5.3 Mm) in TFA, there was added, under ice-cooling, a 1M solution of trifluoromethanesulfonic acid-thioanisole-m-cresol in TFA to react these for one hour and then the protective groups present on the side chains and termini of the peptide were removed. The reaction solution was poured into ether, the resulting oily precipitates were dissolved in distilled water, then washed with ethyl acetate, passed through a column packed with an anion-exchange resin (Amberlite IRA-400Cl Type) to thus convert into hydrochloride and lyophilized to give 2.17 g (yield 86%) of a white solid.

| Amino Acid Analysis (nmol/50μ l) | |
| --- | --- |
| Arg | 4.9877 |
| Gly | 10.3916 |
| Asp | 5.0199 |
| Ser | 4.8891 |
| Mass Spectra: M+ 404 | |

Preparation Example 3: Synthesis of Peptide-6: H-(Gly-Arg-Gly-Asp-Ser-Pro)-OH (SEQ ID NO:6)

Synthesis of this peptide was performed using a peptide synthesizer according to the Merrifield System. α-Amino groups were protected with Boc, the resulting peptide was purified by preparative HPLC after separating from the solid phase of a resin to give an adhesive synthetic peptide showing a single peak (yield 25%).

Example 1: Synthesis of CM-Chitin-Arg-Gly-Asp-Ser (SEQ ID NO: 7)

There was dissolved, in a phosphate buffer of Ph 7.4, 0.30 g of a CM-chitin (available from Yaizu Fishery Chemical Industries, Ltd.) having a viscosity of 9 cps (1% solution at 20° C.), a degree of etherification of 0.78 and a degree of deacetylation of 0.5 and a solution of 128 mg of water-soluble DCC [1-ethyl-3,3-(dimethylaminopropyl)-carbodiimide] in 2.6 ml of a phosphate buffer was added thereto while maintaining the temperature at 0° C. to perform the reaction for 1.5 hour. Then a solution of 400 mg of an adhesive peptide: Arg-Gly-Asp-Ser (SEQ ID NO: 7) (available from Teikoku Chemical Industries Co., Ltd.) in 8 ml of a phosphate buffer was added to the reaction solution and the reaction was continued at 4° C. overnight. The reaction solution was packed in a Visking tube, purified through dialysis against deionized water and then pure water to remove the low molecular weight components and then lyophilized (yield 0.24 g). The structure of the product was confirmed by IR and the analysis of amino acid sequence.

| Amino Acid Analysis (nmol/50μ l) | |
|---|---|
| glucosamine | 20.5558 |
| Arg | 2.0556 |
| Gly | 2.1352 |
| Asp | 1.9854 |
| Ser | 1.8792 |

The rate of introduction of Arg-Gly-Asp-Ser (SEQ ID NO: 7) fragments was determined from the ratio of the concentration of arginine residue to that of glucosamine in accordance with the following relation and found to be about 10%.

Rate of Introduction = [Arg] / [glucosamine] × 100

IR: stretching vibration of amidocarbonyl (C=O) 1652 cm$^{-1}$

Example 2: Synthesis of Succinylated CM-Chitin-Arg-Gly-Asp-Ser (SEQ ID NO: 7)

There was dissolved, in 100 ml of a 1% triethylamine solution, 20.0 g of the CM-chitin used in Example 1, 34.0 g of succinic anhydride and 2.00 g of 4-dimethylaminopyridine were added to the resulting solution and the mixture was stirred at room temperature for a day and night. After completion of the reaction, the solution was poured into a large excess of acetone to again precipitate the succinylated CM-chitin. After collecting the precipitates, the precipitates were washed with a large amount of methanol and then ether and dried in vacuo. Yield = 22.40 g.

There was dissolved, in a phosphate buffer of Ph 7.4, 0.30 g of the succinylated CM-chitin and a solution of 128 mg of water-soluble DCC [1-ethyl-3,3-(dimethylaminopropyl)-carbodiimide] in 2.6 ml of a phosphate buffer was added thereto while maintaining the temperature at 0° C. to continue the reaction for 1.5 hour. Then a solution of 400 mg of Arg-Gly-Asp-Ser (SEQ ID NO:7) in 8 ml of a phosphate buffer was added to the reaction solution and the reaction was continued at 4° C. overnight. The reaction solution was packed in a Visking tube, purified through dialysis against deionized water and then pure water to remove the low molecular weight components and then lyophilized (yield 0.26 g).

The structure of the product was confirmed by IR and the analysis of amino acid sequence. As a result of the amino acid sequence analysis, the rate of introduction of Arg-Gly-Asp-Ser (SEQ ID NO: 7) fragment was found to be about 10%.

The structural formula of the succinylated CM-chitin-Arg-Gly-Asp-Ser SEQ ID NO: 7) is as follows:

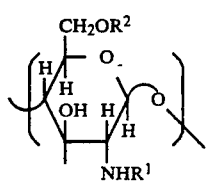

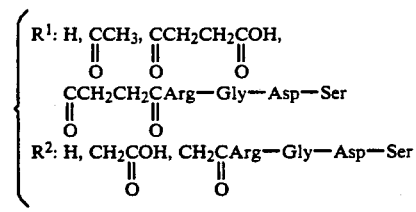

| Succinylated CM—Chitin Arg—Gly—Asp—Ser (SEQ ID NO: 7) | |
|---|---|
| Amino Acid Analysis | (nmole/50μ l) |
| glucosamine | 23.6218 |
| Arg | 2.3622 |
| Gly | 2.1253 |
| Asp | 2.2391 |
| Ser | 2.0031 |

Stretching vibration of amidocarbonyl (C=O) 1652 cm$^{-1}$

Example 3: Synthesis of Maleyl Derivative of CM-Chitin Arg-Gly-Asp-Ser (SEQ ID NO: 7)

The same procedures used in Example 2 were repeated except that 20.00 g of the CM-chitin obtained in Example 1 and 36.6 g of maleic anhydride were reacted to give 21.60 g of maleyl derivative of CM-chitin.

The maleyl derivative of CM-chitin (0.30 g) was dissolved in a phosphate buffer of Ph 7.4 and then Arg-Gly-Asp-Ser (SEQ ID NO: 7) fragments were covalently bonded to the CM-chitin derivative in the same manner used in Example 2 (yield 0.33 g).

The structure of the product was confirmed by IR and the analysis of amino acid sequence. As a result of the amino acid sequence analysis, the rate of introduction of Arg-Gly-Asp-Ser (SEQ ID NO: 7) fragment was found to be about 11%.

| Maleyl Derivative of CM—Chitin Arg—Gly—Asp—Ser (SEQ ID NO: 7) | |
|---|---|
| Amino Acid Analysis | (nmole/50μ l) |
| glucosamine | 28.4956 |
| Arg | 3.1345 |
| Gly | 2.7751 |
| Asp | 2.7213 |
| Ser | 2.5694 |

IR: stretching vibration of amidocarbonyl (C=O) 1648 cm$^{-1}$

Example 4: Synthesis of Phthaloyl derivative of CM-Chitin Arg-Gly-Asp-Ser (SEQ ID NO: 7)

The same procedures used in Example 2 were repeated except that 20.00 g of the CM-chitin obtained in Example 1 and 50.0 g of phthalic anhydride were reacted to give 22.31 g of phthaloyl derivative of CM-chitin. The phthaloyl derivative of CM-chitin (0.30 g) was dissolved in a phosphate buffer of pH 7.4 and then Arg-Gly-Asp-Ser (SEQ ID NO: 7) fragments were covalently bonded to the CM-chitin derivative in the same manner used in Example 2 (yield 0.44 g).

The structure of the product was confirmed by IR and the analysis of amino acid sequence. As a result of the amino acid sequence analysis, the rate of introduction of Arg-Gly-Asp-Ser (SEQ ID NO: 7) fragment was found to be about 12%.

| Phthaloyl Derivative of CM—Chitin Arg—Gly—Asp—Ser (SEQ ID NO: 7) | |
|---|---|
| Amino Acid Analysis | (nmole/50μ 1) |
| glucosamine | 19.1856 |
| Arg | 2.3023 |
| Gly | 2.2231 |
| Asp | 1.8937 |
| Ser | 1.7632 |

IR: stretching vibration of amidocarbonyl (C=O) 1652 cm$^{-1}$

Example 5: Synthesis of Itaconyl Derivative of CM-Chitin Arg-Gly-Asp-Ser (SEQ ID NO: 7)

The same procedures used in Example 2 were repeated except that 20.00 g of the CM-chitin obtained in Example 1 and 38.0 g of itaconic anhydride were reacted to give 21.45 g of itaconyl derivative of CM-chitin.

The itaconyl derivative of CM-chitin (0.30 g) was dissolved in a phosphate buffer of pH 7.4 and then Arg-Gly-Asp-Ser (SEQ ID NO: 7) fragments were covalently bonded to the CM-chitin derivative in the same manner used in Example 2 (yield 0.36 g).

The structure of the product was confirmed by IR and the analysis of amino acid sequence. As a result of the amino acid sequence analysis, the rate of introduction of Arg-Gly-Asp-Ser (SEQ ID NO: 7) fragment was found to be about 9%.

| Itaconyl Derivative of CM—Chitin Arg—Gly—Asp—Ser (SEQ ID NO: 7) | |
|---|---|
| Amino Acid Analysis | (nmole/50μ 1) |
| glucosamine | 35.2316 |
| Arg | 3.1708 |
| Gly | 3.2511 |
| Asp | 3.1005 |
| Ser | 2.8862 |

IR: stretching vibration of amidocarbonyl (C=O) 1650 cm$^{-1}$

Example 6: Synthesis of Trimellityl Derivative of CM-Chitin Arg-Gly-Asp-Ser (SEQ ID NO: 7)

The same procedures used in Example 2 were repeated except that 20.00 g of the CM-chitin obtained in Example I and 64.9 g of trimellitic anhydride were reacted to give 23.75 g of trimellityl derivative of CM-chitin.

The trimellityl derivative of CM-chitin (0.30 g) was dissolved in a phosphate buffer of pH 7.4 and then Arg-Gly-Asp-Ser (SEQ ID NO: 7) fragments were covalently bonded to the CM-chitin derivative in the same manner used in Example 2 (yield 0.37 g).

The structure of the product was confirmed by IR and the analysis of amino acid sequence. As a result of the amino acid sequence analysis, the rate of introduction of Arg-Gly-Asp-Ser (SEQ ID NO: 7) fragment was found to be about 14%.

| Trimellityl Derivative of CM—Chitin Arg—Gly—Asp—Ser (SEQ ID NO: 7) | |
|---|---|
| Amino Acid Analysis | (nmole/50μ 1) |
| glucosamine | 18.7612 |
| Arg | 2.6266 |
| Gly | 2.7899 |
| Asp | 2.5532 |
| Ser | 2.2689 |

IR: stretching vibration of amidocarbonyl (C=O) 1656 cm$^{-1}$

Example 7: Synthesis of CM-Chitin Gly-Arg-Gly-Asp-Ser (SEQ ID NO: 8)

The same procedures used in Example 1 were repeated except that 460 mg of Gly-Arg-Gly-Asp-Ser (SEQ ID NO: 8) (available from Kokusan Chemical Industries Co., Ltd.) was used as the cohesive peptide fragment to give 0.36 g of CM-chitin Gly-Arg-Gly-Asp-Ser (SEQ ID NO: 8).

The structure of the product was confirmed by IR and the analysis of amino acid sequence. As a result of the amino acid sequence analysis, the rate of introduction of Gly-Arg-Gly-Asp-Ser (SEQ ID NO: 8) fragment was found to be about 10%.

| CM—Chitin Gly—Arg—Gly—Asp—Ser (SEQ ID NO: 8) | |
|---|---|
| Amino Acid Analysis | (nmole/50μ 1) |
| glucosamine | 15.3319 |
| Arg | 1.5332 |
| Gly | 3.2132 |
| Asp | 1.3468 |
| Ser | 1.1132 |

IR: stretching vibration of amidocarbonyl (C=O) 1654 cm$^{-1}$

Example 8: Synthesis of Succinylated CM-Chitin Gly-Arg-Gly-Asp-Ser (SEQ ID NO: 8)

The same procedures used in Example 2 were repeated except that 460 mg of Gly-Arg-Gly-Asp-Ser was used as the adhesive peptide fragment to give 0.39 g of succinylated CM-chitin Gly-Arg-Gly-Asp-Ser (SEQ ID NO: 8).

The structure of the product was confirmed by IR and the analysis of amino acid sequence. As a result of the amino acid sequence analysis, the rate of introduction of Gly-Arg-Gly-Asp-Ser (SEQ ID NO: 8) fragment was found to be about 12%.

| Succinylated CM—Chitin-Gly—Arg—Gly—Asp—Ser (SEQ ID NO: 8) | |
|---|---|
| Amino Acid Analysis | (nmole/50μ 1) |
| glucosamine | 30.3268 |
| Arg | 3.6392 |
| Gly | 7.0624 |
| Asp | 3.5691 |
| Ser | 3.3006 |

IR: stretching vibration of amidocarbonyl (C=O) 1648 cm$^{-1}$

Example 9: Synthesis of Succinylated CM-Chitin Arg-Gly-Asp (SEQ ID NO: 1)

The same procedures were used in Example 2 were repeated except that 460 mg of Arg-Gly-Asp was used as the adhesive peptide fragment to give 0.34 of succinylated CM-chitin-Arg-Gly-Asp (SEQ ID NO: 1).

The structure of the product was confirmed by IR and the analysis of amino acid sequence. As a result of the amino acid sequence analysis, the rate of introduction of Arg-Gly-Asp (SEQ ID NO: 1) fragment was found to be about 16%.

| Succinylated CM—Chitin-Arg—Gly—Asp (SEQ ID NO: 1) | |
|---|---|
| Amino Acid Analysis | (nmole.50µ 1) |
| glucosamine | 27.8867 |
| Arg | 4.4619 |
| Gly | 4.5518 |
| Asp | 4.4911 |

IR: stretching vibration of amidocarbonyl (C=O) 1650 cm$^{-1}$

Example 10: Synthesis of Succinylated CM-Chitin-(Arg-Gly-Asp)$_2$ (SEQ ID NO: 2)

The same procedures used in Example 2 were repeated except that 460 mg of (Arg-Gly-Asp)$_2$ (SEQ ID NO:2) was used as the cohesive peptide fragment to give 0.31 g of succinylated CM-chitin-(Arg-Gly-Asp)$_2$ (SEQ ID NO: 2).

The structure of the product was confirmed by IR and the analysis of amino acid sequence. As a result of the amino acid sequence analysis, the rate of introduction of (Arg-Gly-Asp)$_2$ (SEQ ID NO: 2) fragment was found to be about 12%.

| Succinylated CM—Chitin-(Arg—Gly—Asp)$_2$ (SEQ ID NO: 2) | |
|---|---|
| Amino Acid Analysis | (nmole/50µ 1) |
| glucosamine | 25.1913 |
| Arg | 6.0459 |
| Gly | 5.9883 |
| Asp | 5.8996 |

IR: stretching vibration of amidocarbonyl (C=O) 1654 cm$^{-1}$

Example 11: Synthesis of Succinylated CM-Chitin-(Arg-Gly-Asp)$_3$ (SEQ ID NO: 3)

The same procedures used in Example 2 were repeated except that 460 mg of (Arg-Gly-Asp)$_3$ (SEQ ID NO: 3) was used as the cohesive peptide fragment to give 0.33 g of succinylated CM-chitin-(Arg-Gly-Asp)$_3$ (SEQ ID NO: 3).

The structure of the product was confirmed by IR and the analysis of amino acid sequence. As a result of the amino acid sequence analysis, the rate of introduction of (Arg-Gly-Asp)$_3$ (SEQ ID NO: 3) fragment was found to be about 10%.

| Succinylated CM—Chitin-(Arg—Gly—Asp)$_3$ (SEQ ID NO: 3) | |
|---|---|
| Amino Acid Analysis | (nmole/50µ 1) |
| glucosamine | 22.3161 |
| Arg | 6.6949 |
| Gly | 6.5132 |
| Asp | 6.2323 |

IR: stretching vibration of amidocarbonyl (C=O) 1648 cm$^{-1}$ Example 12: Synthesis of Succinylated CM-Chitin-(Arg-Gly-Asp)$_5$ (SEQ ID NO: 4)

The same procedures used in Example 2 were repeated except that 460 mg of (Arg-Gly-Asp)$_5$ (SEQ ID NO: 4) was used as the cohesive peptide fragment to give 0.28 g of succinylated CM-chitin-(Arg-Gly-Asp)$_5$ (SEQ ID NO: 4).

The structure of the product was confirmed by IR and the analysis of amino acid sequence. As a result of the amino acid sequence analysis, the rate of introduction of (Arg-Gly-Asp)$_5$ (SEQ ID NO: 4) fragment was found to be about 15%.

| Succinylated CM—Chitin-(Arg—Gly—Asp)$_5$ (SEQ ID NO: 4) | |
|---|---|
| Amino Acid Analysis | (nmole/50µ 1) |
| glucosamine | 23.6811 |
| Arg | 23.0108 |
| Gly | 21.0993 |
| Asp | 20.3332 |

IR: stretching vibration of amidocarbonyl (C=O) 1656 cm$^{-1}$

Example 13: Synthesis of Sulfated CM-Chitin-Arg-Gly-Asp-Ser (SEQ ID NO: 7)

A CM-chitin having a degree of etherification of 0.50 and a degree of deacetylation of 0.05 was sulfated according to the Tokura's method (Jpn. J. Cancer Res., 1989, 80, pp. 866–872; Cancer Res., 1990 50, pp. 3631–3637) and then Arg-Gly-Asp-Ser (SEQ ID NO: 7) fragments were covalently bonded to the sulfated CM-chitin in the same manner were used in Example 1 (yield 0.36 g).

The structure of the product was confirmed by IR and the analysis of amino acid sequence. As a result of the amino acid sequence analysis, the rate of introduction of Arg-Gly-Asp-Ser (SEQ ID NO: 7) fragment was found to be about 12%.

| Sulfated CM—Chitin-Arg—Gly—Asp—Ser (SEQ ID NO: 7) | |
|---|---|
| Amino Acid Analysis | (nmole/50µ 1) |
| glucosamine | 33.1569 |
| Arg | 3.9780 |
| Gly | 3.9251 |
| Asp | 3.6053 |
| Ser | 3.4921 |

IR: stretching vibration of amidocarbonyl (C=O) 1650 cm$^{-1}$

Example 14: Synthesis of Sulfated CM-Chitin-Gly-Arg-Gly-Asp-Ser (SEQ ID NO: 8)

In the same manner used in Example 1, 460 mg of Gly-Arg-Gly-Asp-Ser (SEQ ID NO: 8) and the sulfated CM-chitin obtained in Example 13 were covalently bonded to give 0.35 g of sulfated CM-chitin-Gly-Arg-Gly-Asp-Ser (SEQ ID NO: 8).

The structure of the product was confirmed by IR and the analysis of amino acid sequence. As a result of the amino acid sequence analysis, the rate of introduction of Gly-Arg-Gly-Asp-Ser (SEQ ID NO: 8) fragment was found to be about 10%.

| Sulfated CM—Chitin-Gly—Arg—Gly—Asp—Ser (SEQ ID NO: 8) | |
|---|---|
| Amino Acid Analysis | (nmole/50µ 1) |
| glucosamine | 25.1515 |
| Arg | 2.51 |
| Gly | 5.2134 |
| Asp | 2.4251 |

-continued

| Sulfated CM—Chitin-Gly—Arg—Gly—Asp—Ser (SEQ ID NO: 8) | |
|---|---|
| Amino Acid Analysis | (nmole/50μ 1) |
| Ser | 2.1111 |

IR: stretching vibration of amidocarbonyl (C=O) 1655 cm$^{-1}$

Example 15: Synthesis of Sulfated Succinylated CM-Chitin-Arg-Gly-Asp-Ser (SEQ ID NO: 7)

In the same manner used in Example 13, the succinylated CM-chitin obtained in Example 2 was sulfated and Arg-Gly-Asp-Ser (SEQ ID NO: 7) fragments were covalently bonded thereto in the same manner used in Example 2 (yield 0.37 g).

The structure of the product was confirmed by IR and the analysis of amino acid sequence. As a result of the amino acid sequence analysis, the rate of introduction of Arg-Gly-Asp-Ser (SEQ ID NO: 7) fragment was found to be about 14%.

| Sulfated Succinylated CM—Chitin-Arg—Gly—Asp—Ser (SEQ ID NO: 7) | |
|---|---|
| Amino Acid Analysis | (nmole/50μ 1) |
| glucosamine | 18.6932 |
| Arg | 2.6170 |
| Gly | 2.7739 |
| Asp | 2.5931 |
| Ser | 2.2168 |

IR: stretching vibration of amidocarbonyl (C=O) 1654 cm$^{-1}$

Example 16: Synthesis of Sulfated Succinylated CM-Chitin-Gly-Arg-Gly-Asp-Ser (SEQ ID NO: 8)

In the same manner used in Example 13, the succinylated CM-chitin obtained in Example 2 was sulfated and Gly-Arg-Gly-Asp-Ser (SEQ ID NO: 8) fragments were covalently bonded thereto in the same manner used in Example 7 (yield 0.31 g).

The structure of the product was confirmed by IR and the analysis of amino acid sequence. As a result of the amino acid sequence analysis, the rate of introduction of Gly-Arg-Gly-Asp-Ser (SEQ ID NO: 8) fragment was found to be about 17%.

| Sulfated Succinylated CM—Chitin Gly—Arg—Gly—Asp—Ser (SEQ ID NO: 8) | |
|---|---|
| Amino Acid Analysis | (nmole/50μ 1) |
| glucosamine | 22.5661 |
| Arg | 3.8362 |
| Gly | 7.4963 |
| Asp | 3.6811 |
| Ser | 3.2593 |

IR: stretching vibration of amidocarbonyl (C=O) 1652 cm$^{-1}$

Example 17: Synthesis of CM-chitin-Arg-Gly-Asp-Ser-Gly-NH$_2$ (SEQ ID NO: 5)

The same procedures used in Example 1 were repeated except that 460 mg of the peptide-5 (Arg-Gly-Asp-Ser-Gly-NH$_2$; Preparation Example 2) (SEQ ID NO: 5) was used as an adhesive peptide fragment to give 0.36 g of CM-chitin Arg-Gly-Asp-Ser-Gly-NH$_2$ (SEQ ID NO: 5).

The structure of the product was confirmed by IR and the analysis of amino acid sequence. As a result of the amino acid sequence analysis, the rate of introduction of Arg-Gly-Asp-Ser-Gly-NH$_2$ (SEQ ID NO: 5) fragment was found to be about 10%.

| CM—Chitin-Arg—Gly—Asp—Ser—Gly—NH$_2$ (SEQ ID NO: 5) | |
|---|---|
| Amino Acid Analysis | (nmole/50μ 1) |
| glucosamine | 17.6368 |
| Arg | 1.8166 |
| Gly | 3.8243 |
| Asp | 1.8468 |
| Ser | 1.6112 |

IR: stretching vibration of amidocarbonyl (C=O) 1658 cm$^{-1}$

Example 18: Synthesis of CM-Chitin Arg-Gly-Asp-Ser (SEQ ID NO: 7)

The same procedures used in Example 1 were repeated except that 1.5 g of Arg-Gly-Asp-Ser (SEQ ID NO: 7) was used as an adhesive peptide fragment to give 0.32 g of CM-chitin-Arg-Gly-Asp-Ser (SEQ ID NO: 7).

The structure of the product was confirmed by IR and the analysis of amino acid sequence. As a result of the amino acid sequence analysis, the rate of introduction of Arg-Gly-Asp-Ser (SEQ ID NO: 7) fragment was found to be about 20%.

| CM—Chitin-Arg—Gly—Asp—Ser (SEQ ID NO: 7) | |
|---|---|
| Amino Acid Analysis | (nmole/50μ 1) |
| glucosamine | 20.4598 |
| Arg | 4.1052 |
| Gly | 4.2688 |
| Asp | 3.9808 |
| Ser | 3.7784 |

IR: stretching vibration of amidocarbonyl (C=O) 1655 cm$^{-1}$

Example 19: Synthesis of CM-Chitin-Gly-Arg-Gly-Asp-Ser-Pro (SEQ ID NO: 6)

The same procedures used in Example 1 were repeated except that 480 mg of Gly-Arg-Gly-Asp-Ser-Pro (SEQ ID NO: 6), i.e., the adhesive peptide fragment-6 (Preparation Example 3) was used as an adhesive peptide fragment to give 0.35 g of CM-chitin-Gly-Arg-Gly-Asp-Ser-Pro (SEQ ID NO: 6).

The structure of the product was confirmed by IR and the analysis of amino acid sequence. As a result of the amino acid sequence analysis, the rate of introduction of Gly-Arg-Gly-Asp-Ser-Pro (SEQ ID NO: 6) fragment was found to be about 10%.

| CM—Chitin-Gly—Arg—Gly—Asp—Ser—Pro (SEQ ID NO: 6) | |
|---|---|
| Amino Acid Analysis | (nmole/50μ 1) |
| glucosamine | 15.3319 |
| Arg | 1.5332 |
| Gly | 3.2132 |
| Asp | 1.3468 |
| Ser | 1.1132 |
| Pro | 1.3326 |

IR: stretching vibration of amidocarbonyl (C=O) 1657 cm$^{-1}$

Test Example 1: Determination of Cell Adhesion-Inhibitory Activity

A method for determining the activity of the CM-chitin derivatives of the present invention for inhibiting adhesion of cells to fibronectin or vitronectin will be described below. The competitive assays used herein have widely been employed tin the field of biochemistry and are detailed in, for instance, "Method in Enzymology", 1981, 82, pp. 803–831; and J. P. KOKAI Nos. Hei 1-309682 and Hei 2-174797.

EXPERIMENTAL METHOD

1. Preparation of Adsorption Plate

Commercially available fibroneotin (derived from human; purchased from Seikaqaku Kogyo K. K.) and vitronectin (derived from human; purchased from Funakoshi Co., Ltd.) each was diluted to 1.0 µl/ml and 2.0 µl/ml with PBS ($NaH_2PO_4$ 0.005 M+NaCl 0.07 M), 0.5 ml of the resulting diluted solution was dispensed into a plastic plate having 24 wells and incubated at 37° C. overnight to perform coating of the plate. Then bovine serum albumin (BSA 1%) was added followed by incubation at 37° C. for one hour for inhibiting the occurrence of nonspecific adsorption, then washing with PBS in the usual manner and sufficient drainage to give an adsorption plate.

2. Adhesion-Inhibitory Test

A CM-chitin derivative obtained through lyophilization was diluted with Dulbecco's Modified Eagles Medium (hereunder referred to as "DMEM") to give solutions of the CM-chitin derivative having concentrations of 0, 0.25, 0.5, 1.0 and 1.5 mg/ml respectively. Each of the solutions (0.25 ml) was dispensed to the plate prepared above, 0.25 ml of a suspension of endothelium cells of blood vessel ($4 \times 10^6$ cells/ml) was added to the plate and incubated at 37° C. for one hour to thus cause cohesion of the cells. The plate was washed three times with DMEM medium to remove non-adhesive cells, then the adhered cells were peeled off with a 0.025% EDTA trypsin solution and stained with a 2% Trypan Blue solution to determine the number of the adhered cells. The results thus obtained are summarized in the following Tables 1 and 2.

TABLE 1

Cell Adhesion-Inhibitory effect Against Fibronectin (cell/well)

| Compound Added | Concentration (mg/ml) | | | | |
|---|---|---|---|---|---|
| | 0 | .25 | 0.5 | 1.0 | 1.5 |
| CM—chitin | 160 | 171 | 157 | 165 | 152 |
| CM—chitin derivative-1 | 160 | 131 | 106 | 79 | 69 |
| CM—chitin derivative-2 | 160 | 135 | 99 | 82 | 75 |
| CM—chitin derivative-3 | 160 | 123 | 100 | 77 | 55 |
| CM—chitin derivative-4 | 160 | 141 | 121 | 80 | 67 |
| CM—chitin derivative-5 | 160 | 136 | 105 | 86 | 72 |
| CM—chitin derivative-6 | 160 | 127 | 107 | 93 | 66 |
| CM—chitin derivative-7 | 160 | 119 | 98 | 84 | 71 |
| CM—chitin derivative-8 | 160 | 130 | 113 | 80 | 59 |
| CM—chitin derivative 9 | 160 | 121 | 97 | 85 | 65 |
| CM—chitin derivative-10 | 160 | 122 | 110 | 87 | 73 |
| CM—chitin derivative-11 | 160 | 143 | 125 | 78 | 70 |
| CM—chitin derivative-12 | 160 | 125 | 101 | 89 | 77 |
| Sulfated CM—chitin | 160 | 150 | 155 | 147 | 141 |
| CM—chitin derivative-13 | 160 | 97 | 77 | 57 | 33 |
| CM—chitin derivative-14 | 160 | 111 | 93 | 68 | 41 |
| CM—chitin derivative-15 | 160 | 105 | 89 | 65 | 37 |
| CM—chitin derivative-16 | 160 | 103 | 81 | 75 | 50 |
| CM—chitin derivative-17 | 160 | 99 | 84 | 61 | 35 |
| CM—chitin derivative-18 | 160 | 133 | 101 | 75 | 52 |
| CM—chitin derivative-19 | 160 | 127 | 106 | 79 | 56 |
| ArgGlyAsp (SEQ ID NO: 1) | 160 | 157 | 162 | 141 | 83 |
| GlyArgGlyAspSer (SEQ ID NO: 8) | 160 | 154 | 140 | 95 | 80 |

TABLE 2

Cell Adhesion-Inhibitory effect Against Vitronectin (cell/well)

| Compound Added | Concentration (mg/ml) | | | | |
|---|---|---|---|---|---|
| | 0 | 10 | 50 | 100 | 300 |
| CM—chitin | 249 | 260 | 243 | 240 | 255 |
| CM—chitin derivative-1 | 249 | 148 | 89 | 72 | 41 |
| CM—chitin derivative-2 | 249 | 137 | 96 | 78 | 59 |
| CM—chitin derivative-3 | 249 | 141 | 87 | 69 | 49 |
| CM—chitin derivative-4 | 249 | 145 | 90 | 67 | 45 |
| CM—chitin derivative-5 | 249 | 129 | 91 | 80 | 48 |
| CM—chitin derivative-6 | 249 | 133 | 98 | 71 | 56 |
| CM—chitin derivative-7 | 249 | 143 | 85 | 79 | 55 |
| CM—chitin derivative-8 | 249 | 130 | 95 | 69 | 47 |
| CM—chitin derivative-9 | 249 | 139 | 88 | 77 | 58 |
| CM—chitin derivative-10 | 249 | 136 | 86 | 71 | 43 |
| CM—chitin derivative-11 | 249 | 147 | 100 | 73 | 45 |
| CM—chitin derivative-12 | 249 | 150 | 101 | 80 | 59 |
| Sulfated CM—chitin | 249 | 231 | 235 | 222 | 200 |
| CM—chitin derivative-13 | 249 | 103 | 70 | 47 | 31 |
| CM—chitin derivative-14 | 249 | 107 | 78 | 43 | 34 |
| CM—chitin derivative-15 | 249 | 115 | 69 | 54 | 38 |
| CM—chitin derivative-16 | 249 | 122 | 81 | 63 | 40 |
| CM—chitin derivative-17 | 249 | 114 | 76 | 48 | 33 |
| CM—chitin derivative-18 | 249 | 125 | 83 | 56 | 44 |
| CM—chitin derivative-19 | 249 | 130 | 92 | 63 | 39 |
| ArgGlyAsp (SEQ ID NO: 1) | 249 | 171 | 132 | 104 | 73 |
| GlyArgGlyAspSer (SEQ ID NO: 8) | 249 | 157 | 116 | 87 | 61 |

Test Example 2: Determination of Platelet Coagulation-Inhibitory Activity

The platelet coagulation-inhibitory effect of the CM-chitin derivative of the present invention was assayed, in vitro, using human plasma rich in platelet. The experimental method will be described below.

EXPERIMENTAL METHOD

To fresh human blood, there was added 1/9 volume of a 3.8% sodium citrate solution, the resulting mixture was centrifuged (1000 rpm; for 10 minutes) and the upper layer was separated as a plasma rich in platelet. A lyophilized CM-chitin derivative was dissolved in physiological saline to give a plurality of solutions having various concentrations ranging from 0 to 1.5 mg/ml. Each of the solutions (25 µl) was added to 200 µl of the plasma, incubated at 37° C. for 3 minutes, then a 50 µM of ADP (adenosine diphosphate) solution or a 200 µg/ml collagen solution was added to determine the extent of coagulation in terms of transmittance determined by an aggregometer. The results thus obtained are listed in the following Table 3.

Rate of Coagulation Inhibition=(1-T/T.)×100%

T.: transmittance observed when a salt of CM-chitin derivative was not added.

T : transmittance observed when a salt of CM-chitin derivative was added.

TABLE 3

Platelet Coagulation-Inhibitory Action

| Compound Added | IC$_{50}$ (μg/ml) ADP Stimulation | IC$_{50}$ (μg/ml) Collagen Stimulation |
| --- | --- | --- |
| CM—chitin | 96 | 90 |
| CM—chitin derivative-1 | 15 | 10 |
| CM—chitin derivative-2 | 18 | 10 |
| CM—chitin derivative-3 | 21 | 7 |
| CM—chitin derivative-4 | 29 | 15 |
| CM—chitin derivative-5 | 17 | 12 |
| CM—chitin derivative-6 | 26 | 11 |
| CM—chitin derivative-7 | 30 | 16 |
| CM—chitin derivative-8 | 24 | 14 |
| CM—chitin derivative-9 | 28 | 9 |
| CM—chitin derivative-10 | 20 | 13 |
| CM—chitin derivative-11 | 21 | 12 |
| CM—chitin derivative-12 | 30 | 8 |
| Sulfated CM—chitin | 72 | 61 |
| CM—chitin derivative-13 | 17 | 7 |
| CM—chitin derivative-14 | 12 | 3 |
| CM—chitin derivative-15 | 15 | 6 |
| CM—chitin derivative-16 | 12 | 2 |
| CM—chitin derivative-17 | 14 | 5 |
| CM—chitin derivative-18 | 21 | 10 |
| CM—chitin derivative-19 | 19 | 5 |
| ArgGlyAsp (SEQ ID NO: 1) | 27 | 22 |
| GlyArgGlyAspSer (SEQ ID NO: 8) | 31 | 18 |

What is claimed is:

1. A CM-chitin derivative or a salt thereof, having, as an essential unit, a cohesive peptide represented by the following general formula (I), bonded to the side chain of CM-chitin, wherein the bond connecting CM-chitin and said peptide is selected from the group consisting of an amido bond, an ester bond, an ether bond and a urethane bond:

$-[R^1]-[CO]-([X]-Arg-Gly-Asp-[Y])_n-[Z]-[R^2]-$ ... (I)(SEQ ID NO: 1)

wherein the bracket [ ] means that the corresponding group or residue in the bracket may be present or absent and if they are present, X and Y each represents an amino acid residue selected from the group consisting of Ser, Gly, Val, Asn and Pro or a peptide residue consisting of at least two of said amino acids; Z represents —O— or —NH—; one of $R^1$ and $R^2$ represents a hydrogen atom, or a substituted or unsubstituted alkyl group having 1 to 9 carbon atoms or an aryl group having 6 to 9 carbon atoms and the other represents a hydrogen atom, a linear or branched alkylene group having 1 to 9 carbon atoms or an arylene group having 6 to 9 carbon atoms wherein the alkylene and arylene groups may have substituents; and n is an integer ranging from 1 to 5.

2. The CM-chitin derivative or salt thereof of claim 1, wherein said derivative or salt thereof has a molecular weight of not more than 200,000.

3. The CM-chitin derivative or salt thereof of claim 2, wherein said derivative or salt thereof has a molecular weight ranging from 3,000 to 100,000.

4. The CM-chitin derivative or salt thereof of claim 1, wherein the substituent of $R^1$ and $R^2$ is at least one member selected from the group consisting of halogen atoms, carbonyl, carboxyl, amino, hydroxyl, sulfo, aryl, nitro and cyano groups, and an unsaturated hydrocarbon group which has a double bond and triple bond.

5. The CM-chitin derivative or salt thereof of claim 1, wherein said derivative or salt thereof is water-soluble at room temperature.

6. The CM-chitin derivative or the salt of claim 1, wherein the CM-chitin is sulfated or carboxylated with succinic anhydride, maleic anhydride, phthalic anhydride, itaconic anhydride, citraconic anhydride, pyromellitic anhydride or trimellitic anhydride.

7. The CM-chitin derivative or salt thereof of claim 1, wherein amino acids included in the adhesive peptide are L-isomers.

8. The CM-chitin derivative or salt thereof of claim 1, wherein the salt is selected from the group consisting of hydrochloride, sulfate, nitrate, phosphate, borate, acetate, trifluoroacetate, trifluoromethanesulfonate, lactate and tartrate.

9. A composition for inhibiting adhesion of animal cells comprising, as an effective component, a pharmaceutically effective amount of at least one member selected from the group consisting of CM-chitin derivatives and salts thereof according to claim 1, and a pharmaceutically acceptable carrier.

10. The composition of claim 9, wherein said composition further comprises a stabilizer.

11. The composition of claim 9, wherein said composition is encapsulated into liposomes.

12. The composition of claim 9, wherein said animal cells are blood platelets.

13. The composition of claim 12, wherein said composition further comprises a stabilizer.

14. The composition of claim 12, wherein said composition is encapsulated into liposomes.

15. A process for inhibiting adhesion of animal cells, comprising administering an effective amount of a CM-chitin derivative, or a salt thereof, having, as an essential unit, a cohesive peptide represented by the following general formula (I), bonded to the side chain of CM-chitin wherein the bond connecting CM-chitin and said peptide is selected from the group consisting of an amido bond, an ester bond, an ether bond and a urethane bond:

$-[R^1]-[CO]-([X]-Arg-Gly-Asp-[Y])_n-[Z]-[R^2]-$ ... (I)(SEQ ID NO: 1)

wherein the bracket [ ] means that the corresponding group or residue in the bracket may be present or absent and if they are present, X and Y each represents an amino acid residue selected from the group consisting of Ser, Gly, Val, Asn and Pro or a peptide residue consisting of two or more of said amino acids; Z represents —O— or —NH—; one of $R^1$ and $R^2$ represents a hydrogen atom, or a substituted or unsubstituted alkyl group having 1 to 9 carbon atoms or an aryl group having 6 to 9 carbon atoms and the other represents a hydrogen atom, a linear or branched alkylene group having 1 to 9 carbon atoms or an arylene group having 6 to 9 carbon atoms wherein the alkylene and arylene groups may have substituents; and n is an integer ranging from 1 to 5.

16. The process of claim 15, wherein the dose administered to a subject of the CM-chitin derivative or salt thereof ranges in an amount of from 0.2 µg/kg to 400 µg/kg.

17. The process of claim 15, wherein said animal cells are blood platelets.

18. The process of claim 17, wherein the dose administered to a subject of the CM-chitin derivative or salt thereof ranges in an amount of from 0.2 µg/kg to 400 µg/kg.

* * * * *